US011027086B2

(12) United States Patent
Bowen

(10) Patent No.: US 11,027,086 B2
(45) Date of Patent: Jun. 8, 2021

(54) ORO-NASAL INHALATION PLETHYSMOGRAPHY MASK EXPOSURE SYSTEM

(71) Applicant: The Government of the United States, as Represented by the Secretary of the Army, Ft. Detrick, MD (US)

(72) Inventor: Larry E. Bowen, Williamsport, MD (US)

(73) Assignee: The Government of the United States as represented by the Secretary of the Army, Ft. Detrick, MD (US)

(*) Notice: Subject to any disclaimer, the term of this patent is extended or adjusted under 35 U.S.C. 154(b) by 263 days.

(21) Appl. No.: 16/076,094

(22) PCT Filed: Feb. 7, 2017

(86) PCT No.: PCT/US2017/016845
§ 371 (c)(1),
(2) Date: Aug. 7, 2018

(87) PCT Pub. No.: WO2017/136856
PCT Pub. Date: Aug. 10, 2017

(65) Prior Publication Data

US 2020/0023152 A1 Jan. 23, 2020

Related U.S. Application Data

(60) Provisional application No. 62/292,354, filed on Feb. 7, 2016, provisional application No. 62/375,168, filed on Aug. 15, 2016.

(51) Int. Cl.
*A61M 16/06* (2006.01)
*A61M 16/08* (2006.01)
(Continued)

(52) U.S. Cl.
CPC ............ *A61M 16/06* (2013.01); *A61B 5/091* (2013.01); *A61B 5/4821* (2013.01); *A61M 16/085* (2014.02); *A61M 2250/00* (2013.01)

(58) Field of Classification Search
CPC .. A61D 7/04; A61D 7/00; A61B 5/091; A61B 5/4821; A61B 5/097; A61M 16/06;
(Continued)

(56) References Cited

U.S. PATENT DOCUMENTS 4,265,239 A * 5/1981 Fischer, Jr. ......... A61M 16/009 128/205.17
4,348,985 A 9/1982 Leong
(Continued)

FOREIGN PATENT DOCUMENTS

CN 104305997 A 1/2015
DE 40 09 067 A1 12/1991
(Continued)

OTHER PUBLICATIONS

Broughton et al., "Effect of Electronic Compensation of Plethysmographic Airway Resistance Measurements," Pediatric Pulmonology, Vo. 42, Jul. 20, 2007, pp. 764-772.
(Continued)

*Primary Examiner* — Justin R Yu
*Assistant Examiner* — Mayisha M Khan
(74) *Attorney, Agent, or Firm* — Leigh Callander

(57) ABSTRACT

In at least one embodiment, a system includes an inhalation source; a plenum in fluid communication with the inhalation source; at least one challenge plethysmography mask in fluid communication with the plenum, for each challenge plethysmography mask including a mask having a cavity to receive at least a nose of a test animal, a delivery conduit in fluid communication with the plenum and the cavity of the mask, at least one exhaust conduit in fluid communication with the
(Continued)

cavity of the mask and the plenum, and a pressure sensor attached to the mask to measure pressure within the cavity of the mask; at least one processor in electrical communication with the at least one pressure sensor, the processor configured to process an output signal of the pressure sensor into respiratory data for each test animal during an exposure study; and an exhaust system in fluid communication with the plenum.

19 Claims, 12 Drawing Sheets

(51) Int. Cl.
*A61B 5/091* (2006.01)
*A61B 5/00* (2006.01)

(58) Field of Classification Search
CPC ............ A61M 16/085; A61M 15/0065; A61M 15/0086; A61M 15/009; A61M 2205/50; A61M 2206/11; A61M 2206/16; A61M 2250/00; A61M 2209/02; A61M 2205/7518; A61M 2230/40; A61M 16/009; A61M 16/0627; A61M 2205/3393; A61M 2205/7509; A61M 2205/7545; A61M 11/001; A61M 11/00; A61M 11/06; A61M 13/00; A61M 11/002; A61M 11/003; A61M 2202/0007; A61M 2202/0028; A61M 2202/02; A61M 16/0003; A61M 2205/33; A01K 1/06; A01K 13/003; A01K 1/00; A01K 7/02; A01K 1/03; A61G 10/00; G01N 33/497; G01N 2001/2244; G01N 2033/4975; G01N 31/223
See application file for complete search history.

(56) References Cited

U.S. PATENT DOCUMENTS

| | | | | |
|---|---|---|---|---|
| 4,402,315 | A | 9/1983 | Tsuda et al. | |
| 4,520,808 | A | 6/1985 | LaBauve | |
| 4,582,055 | A * | 4/1986 | McDougal | A61D 7/04 128/202.12 |
| 4,649,911 | A * | 3/1987 | Knight | A61M 15/00 128/200.21 |
| 4,710,887 | A | 12/1987 | Ho | |
| 4,721,060 | A | 1/1988 | Cannon et al. | |
| 4,781,146 | A | 11/1988 | Spengler | |
| 4,860,741 | A | 8/1989 | Bernstein et al. | |
| 5,025,619 | A | 6/1991 | Cannon | |
| 5,109,797 | A | 5/1992 | Briant et al. | |
| 5,156,776 | A | 10/1992 | Loedding et al. | |
| 5,297,502 | A * | 3/1994 | Jaeger | A01K 1/031 119/420 |
| 5,320,108 | A | 6/1994 | Cloutier | |
| 5,379,777 | A | 1/1995 | Lomask | |
| 5,487,378 | A | 1/1996 | Robertson et al. | |
| 5,887,586 | A | 3/1999 | Dahlback et al. | |
| 5,896,829 | A * | 4/1999 | Rothenberg | A61D 7/04 119/417 |
| 6,016,803 | A | 1/2000 | Volberg et al. | |
| 6,131,571 | A | 10/2000 | Lampotang et al. | |
| 6,224,560 | B1 | 5/2001 | Gazula et al. | |
| 6,725,859 | B1 | 4/2004 | Rothenberg et al. | |
| 6,904,912 | B2 | 6/2005 | Roy et al. | |
| 7,377,276 | B2 | 5/2008 | Roy et al. | |
| 7,527,021 | B2 | 5/2009 | Mead et al. | |
| 7,614,280 | B1 * | 11/2009 | Gardner | A62B 27/00 73/38 |
| 8,221,329 | B2 * | 7/2012 | Hartings | A01K 1/031 600/300 |
| 8,985,100 | B2 | 3/2015 | Minocchieri et al. | |
| 9,180,263 | B2 | 11/2015 | Gumaste et al. | |
| 2002/0103443 | A1 * | 8/2002 | Roy | A61D 7/04 600/532 |
| 2003/0055354 | A1 * | 3/2003 | Roy | A61B 5/4845 600/532 |
| 2003/0062042 | A1 * | 4/2003 | Wensley | A61K 31/519 128/203.12 |
| 2004/0216737 | A1 * | 11/2004 | Anderson | A61M 16/1015 128/203.12 |
| 2009/0013997 | A1 * | 1/2009 | Barnewall | A61D 7/04 128/203.15 |
| 2009/0211534 | A1 * | 8/2009 | Schenkel | A61D 7/04 119/420 |
| 2010/0263666 | A1 * | 10/2010 | Nagata | A61M 15/00 128/203.14 |
| 2011/0000481 | A1 | 1/2011 | Gumaste et al. | |
| 2011/0000482 | A1 * | 1/2011 | Gumaste | A61D 7/04 128/200.23 |
| 2013/0255678 | A1 | 10/2013 | Gumaste et al. | |
| 2014/0020687 | A1 | 1/2014 | Cullen et al. | |
| 2014/0058214 | A1 * | 2/2014 | Woodward | A01K 1/031 600/301 |
| 2014/0069426 | A1 * | 3/2014 | Houts | A61D 3/00 128/203.29 |
| 2015/0216643 | A1 * | 8/2015 | Stevens | A61M 16/18 128/203.12 |
| 2018/0228990 | A1 * | 8/2018 | Cole | A61M 15/0066 |

FOREIGN PATENT DOCUMENTS

| | | | |
|---|---|---|---|
| JP | 2-177955 | A | 7/1990 |
| WO | 96/00046 | A1 | 1/1996 |
| WO | 96/13294 | A1 | 5/1996 |
| WO | 02/060336 | A1 | 8/2002 |
| WO | 03/101339 | A1 | 12/2003 |
| WO | 2004/071330 | A2 | 8/2004 |

OTHER PUBLICATIONS

Decker et al., abstract for “A Method for Measuring Respiratory Volume Parameters of Large Animals During Exposure to Aerosols,” American Industrial Hygiene Association Journal, vol. 40, No. 7, 1979, printed from www.tandfonline.com/doi/abs/10.1080/15298667991430000 on Nov. 30, 2015.
Hartings et al., “The Automated Bioaersol Exposure System: Preclinical Platform Development and a Respiratory Dosimetry Application With Nonhuman Primates,” Journal of Pharmacological and Toxicological Methods, vol. 49, 2004, pp. 39-55.
Espacenet, English Abstract of CN104305997.
Espacenet, English Abstract of DE4009067.
Espacenet, English Abstract of JP02177955.
U.S. Patent and Trademark Office, International Search Report in PCT App. No. PCT/US2017/016845, dated Apr. 20, 2017.
U.S. Patent and Trademark Office, Written Opinion in PCT App. No. PCT/US2017/016845, dated Apr. 20, 2017.

* cited by examiner

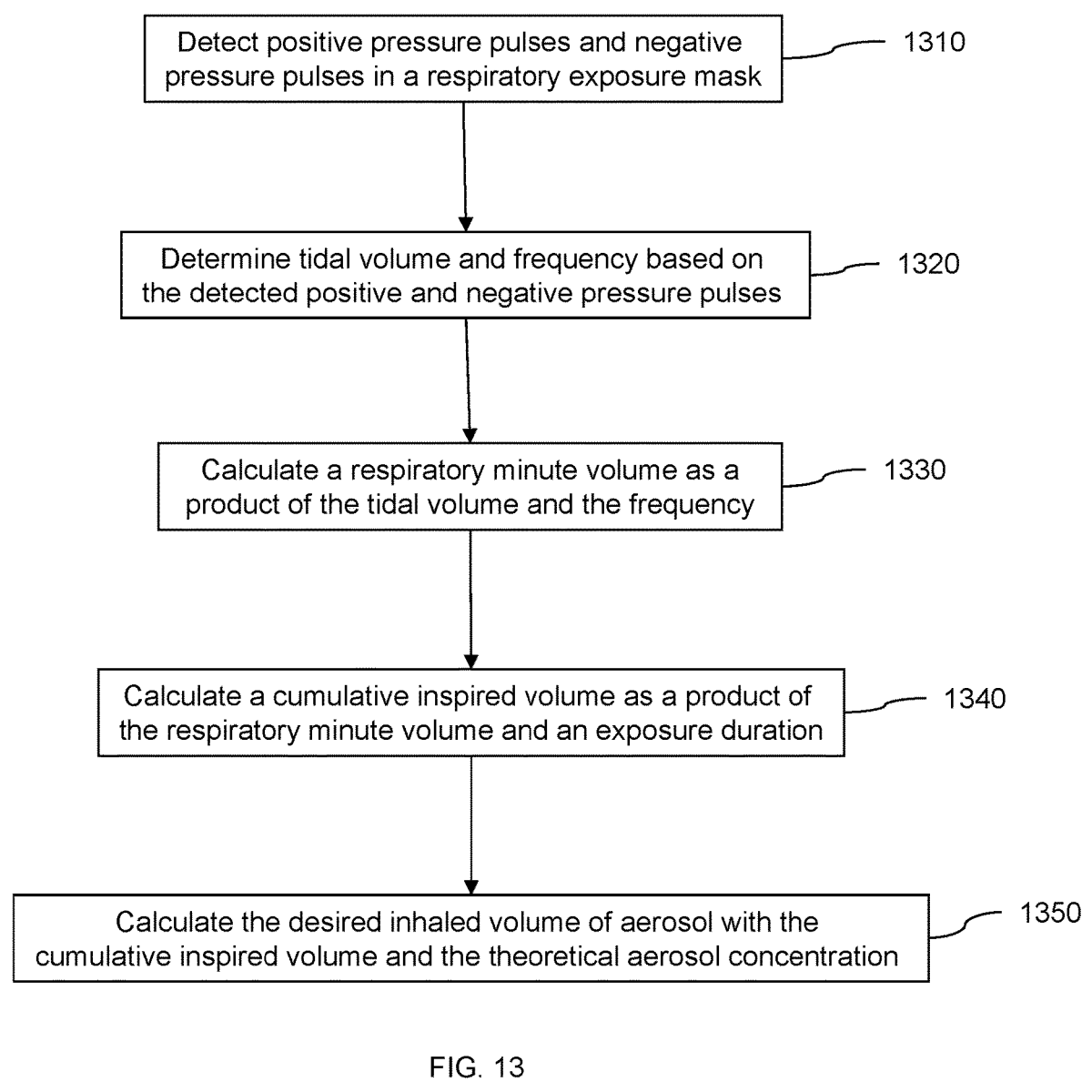

Detect positive pressure pulses and negative pressure pulses in a respiratory exposure mask — 1310

Determine tidal volume and frequency based on the detected positive and negative pressure pulses — 1320

Calculate a respiratory minute volume as a product of the tidal volume and the frequency — 1330

Calculate a cumulative inspired volume as a product of the respiratory minute volume and an exposure duration — 1340

Calculate the desired inhaled volume of aerosol with the cumulative inspired volume and the theoretical aerosol concentration — 1350

FIG. 13

ORO-NASAL INHALATION PLETHYSMOGRAPHY MASK EXPOSURE SYSTEM

This application is the national stage application of PCT international application no. PCT/US2017/016845, filed on 7 Feb. 2017, which claims the benefit of U.S. Patent Application Ser. No. 62/292,354 filed on 7 Feb. 2016 with the U.S. Patent and Trademark Office, which is hereby incorporated by reference.

This invention was made with support from the United States Department of the Army. The United States Government has certain rights in this invention.

I. FIELD OF THE INVENTION

This invention relates to a system having a challenge plethysmography mask for an animal in fluid communication with a plenum where the challenge plethysmography mask includes an inlet, a pair of outlets and at least one sensor for measuring pressure within the mask cavity. The invention further relates to a method for using such a system.

II. BACKGROUND OF THE INVENTION

Oro-nasal (face) masks have been used for many years to deliver anesthetic gases and test articles by inhalation to animals. Correspondingly, several methods are available to determine respiratory parameters in animals including whole-body plethysmography, head-out plethysmography (body-only), and respiratory inductance plethysmography (RIP). There have been efforts to develop and refine the plethysmography equipment and procedures mentioned above to collect respiratory parameters in real-time during inhalation exposure. However, each of these systems present issues that may compromise plethysmography and study data integrity. For instance, whole-body plethysmography is generally practical for rodent species only and would introduce undesirable dermal and ocular contamination when used with nonhuman primates and rabbits. Nonhuman primate head-out plethysmographs have been interfaced with head-only inhalation exposure chambers but these systems are cumbersome, space consuming, and prone to leakage. Commercially available rabbit head-out plethysmographs have slanted face plates that will not interface with head-only inhalation exposure systems. Head-out plethysmography has also been conducted independently and just prior to inhalation exposure. However, pre-exposure plethysmography may be highly variable and is dependent, at least in part, on the anesthetic used and the duration of anesthesia. Therefore, this procedure is likely non-defensible from a Good Laboratory Practice perspective. RIP is a relatively new method of collecting respiratory parameters during nonhuman primate and rabbit inhalation exposures. However, RIP; was found to underestimate lung volumes at the start of inspiration and overestimate lung volume at the end of inspiration in human patients (Stromberg et al., 1993). It is not clear if this artifact is present when used with animals. Additionally, the accuracy of respiratory parameters as derived from thoracic and abdominal bands, is subject to natural variability in the relative rib-cage-to-abdomen contribution, placement on the subject and supine versus sitting positional effects. Another limitation of RIP technology, from an inhalation exposure point of view, is that the system must be calibrated for each animal.

III. SUMMARY OF THE INVENTION

The oro-nasal inhalation plethysmography mask exposure system was designed to combine inhalation exposure with real-time plethysmography. The system in at least one embodiment eliminates the need for head-out plethysmographs and respiratory inductance plethysmography. In at least one embodiment, the system reduces dermal contamination and eliminates ocular contamination.

Challenge plethysmography masks fitted with a differential pressure transducer and signal amplifier according to at least one embodiment were calibrated using certified traceable gas tight syringes. Simulated respiratory volumes of air were introduced into the mask and the resulting waveforms were recorded and analyzed with and without an aerosol present. To confirm the functionality of collecting respiratory tidal volume and frequency, side-by-side comparative tests between the challenge plethysmography mask and a head-out plethysmograph were conducted.

In order to demonstrate the capability of the system built according to at least one embodiment to generate and deliver conditioned, respirable aerosol, it was characterized using a battery of standard tests. An aerosolized saline solution was used to determine time-to-99% steady state equilibrium concentration ($T_{99}$), spatial variation (percent coefficient variation) between the challenge plethysmography and sampling masks aerosol concentrations, and the aerosol particle size distribution at the masks. This disclosure describes the components, procedures and results from the development of this novel system.

In at least one embodiment, a system includes an inhalation source; a plenum in fluid communication with the inhalation source; at least one challenge plethysmography mask in fluid communication with the plenum, for each challenge plethysmography mask having a mask having a cavity in which to receive at least a nose (or a snout) of a test animal, a delivery conduit in fluid communication with the plenum and the cavity of the mask, at least one exhaust conduit in fluid communication with the cavity of the mask and the plenum, and a pressure sensor attached to the mask to measure pressure within the cavity of the mask; at least one processor in electrical communication with the at least one pressure sensor, the processor configured to process an output signal of the pressure sensor into respiratory data for each test animal during an exposure study; and an exhaust system in fluid communication with the plenum.

Further to the previous embodiment, the system further includes at least one sampling mask system in fluid communication with the plenum and in electrical communication with the at least one processor. Further to the previous embodiment, the at least one sampling mask system includes a size sampling mask in fluid communication with the plenum; and an aerosol diluter/APS in fluid communication with the sampling mask and in electrical communication with the at least one processor. Further to the other embodiments of this paragraph, the at least one sampling mask system includes a concentration sampling mask in fluid communication with the plenum; an aerosol sampler in fluid communication with the concentration sampling mask; at least one filter in fluid communication with the aerosol sampler and the exhaust system. Further to the previous embodiment, the size sampling mask and the concentration sampling mask includes a mask having a cavity, a delivery conduit in fluid communication with the plenum and the cavity of the mask, a pair of exhaust conduits in fluid communication with the cavity of the mask and the plenum, the exhaust conduits are located on opposing surfaces of the mask, a sealing wall covering an open side of the mask, and a sampling conduit passing through the sampling wall and placing a sampling end at a point inside the cavity of the mask and an attachment end is external to the mask.

Further to any of the previous embodiments, the inhalation source includes a compressed gas source; a gas flow controller in fluid communication with the compressed gas source; and a nebulizer in fluid communication with the gas flow controller and the plenum. Further to the previous embodiment, the inhalation source further includes a second gas flow controller in fluid communication with the compressed gas source; and a radial mixer in fluid communication with the nebulizer, the second gas flow controller and the nebulizer such that the gas flows from the nebulizer and the second gas flow controller are mixed together prior to discharge towards the plenum. Further to the previous two embodiments, the inhalation source further includes a diffusion dryer in fluid communication with the plenum such that the gas flow from the inhalation source passes through it prior to entry into the plenum.

Further to any of the above embodiments, the exhaust system includes at least one filter in fluid communication with the plenum; an exhaust gas flow controller in fluid communication with the plenum such that the exhaust gas flow controller regulates the flow rate exiting the plenum; and a vacuum in fluid communication with the exhaust gas flow controller to draw the exiting gas flow from the plenum. Further to any of the above embodiments, each challenge plethysmography mask having two exhaust conduits attached on opposing surfaces of the mask. Further to the previous embodiments, the two exhaust conduits from a Y-shaped conduit such that the stem of the Y is in fluid communication with the plenum. Further to any of the above embodiments, the at least one challenge plethysmography mask includes a dental dam over at least a portion of an open side of the mask and partially enclosing the cavity of the mask.

According to at least one embodiment, a challenge plethysmography mask for use in an exposure system includes a mask having an open ended cavity in which to receive a snout of a test animal, a delivery conduit connectable to a plenum and in fluid communication with the cavity of the mask, at least one exhaust conduit in fluid communication with the cavity of the mask and connectable to the plenum, and a pressure sensor attached to the mask to measure pressure within the cavity of the mask.

According to at least one embodiment, a method for performing an exposure study of at least one test animal using an exposure system includes placing the snout of one test animal into a challenge plethysmography mask having a delivery conduit connecting the mask to a plenum, at least one exhaust conduit connecting the mask to the plenum, and a pressure sensor on the mask to measure a pressure within the cavity of the mask; creating an environment within the plenum having material provided by an inhalation source where the material is being used in the exposure study; passing the environment through the delivery conduit to the mask; passing the environment in the mask including expiration from the test animal through the at least one exhaust conduit to the plenum; sending a pressure signal from the pressure sensor to a processor; sampling characteristics of the environment present in the plenum; and calculating, with the processor connected to the pressure sensor, a dosage received by the test animal based on respiration data obtained from the pressure signal provided by the pressure sensor and environment characteristics. In a further method embodiment, the sampling of environment characteristics is done intermittently on a predetermined schedule or substantially continuously. In a further method embodiment, sampling characteristics includes sampling a concentration of a material being used in the exposure study. In a further method embodiment, calculating the dosage includes calculating the respiratory frequency for the test animal based on the pressure signal from the pressure sensor, calculating a minute volume based on the respiratory frequency and a tidal volume, correlating the characterization data for the environment with the respiratory information, and determining the dosage received by the test animal. In a further method embodiment, the characterization data includes particle size for the material. In a further embodiment, the method further includes creating the environment using a nebulizer attached to a compressed gas source; and pulling the environment from the plenum using a vacuum.

In at least one embodiment, the method embodiments can be used with the various system embodiments and the system embodiments can be used with the various method embodiments.

Given the following enabling description of the drawings, the invention should become evident to a person of ordinary skill in the art.

IV. BRIEF DESCRIPTION OF THE DRAWINGS

FIG. 13 is a flow diagram illustrating a method for controlling aerosol respiratory exposure according to an embodiment of the invention.

V. DETAILED DESCRIPTION OF THE DRAWINGS

FIGS. 1-5 illustrate different aspects of different embodiments according to the invention.

Figure 1:
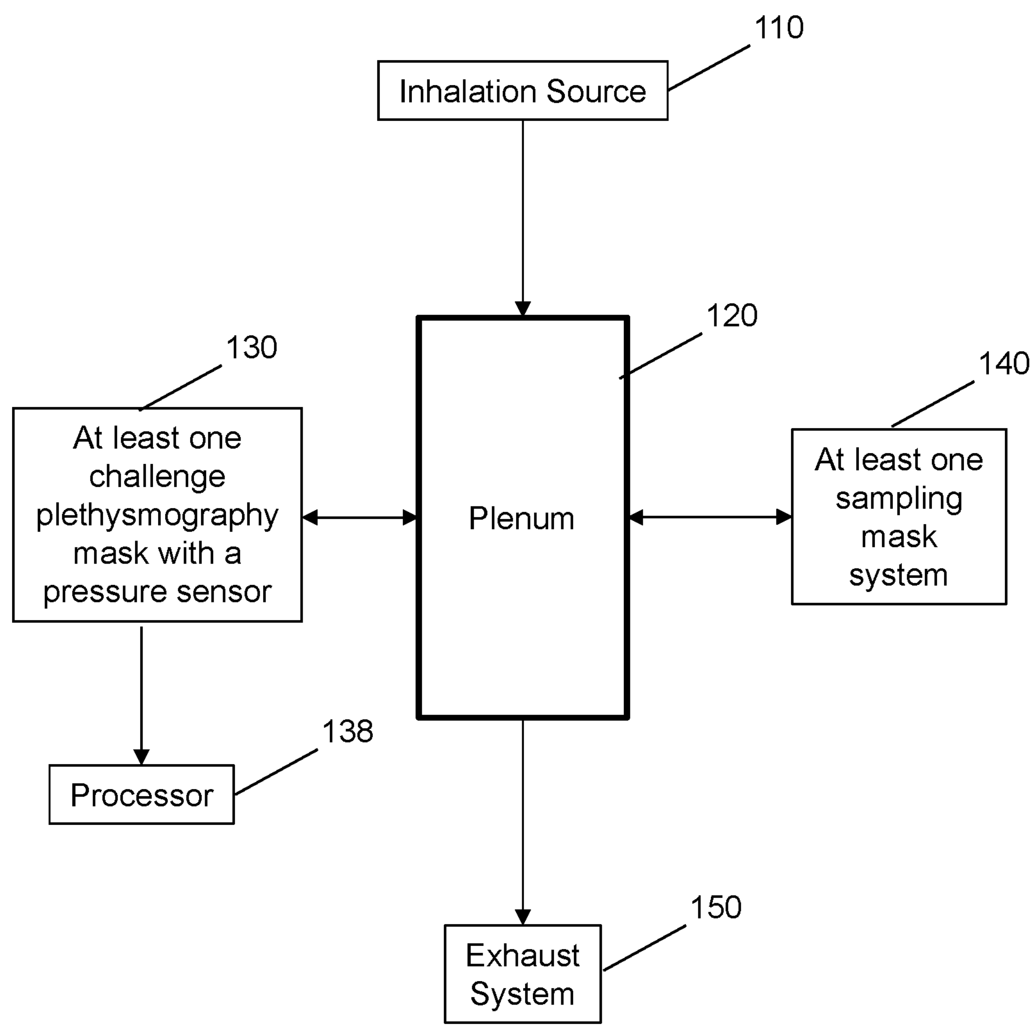
FIG. 1 illustrates a block diagram according to at least one embodiment of the invention.

FIG. 1 illustrates a system having an inhalation source 110, which provides the test article or material being used in the exposure study, in fluid communication with a plenum

Figure 2:
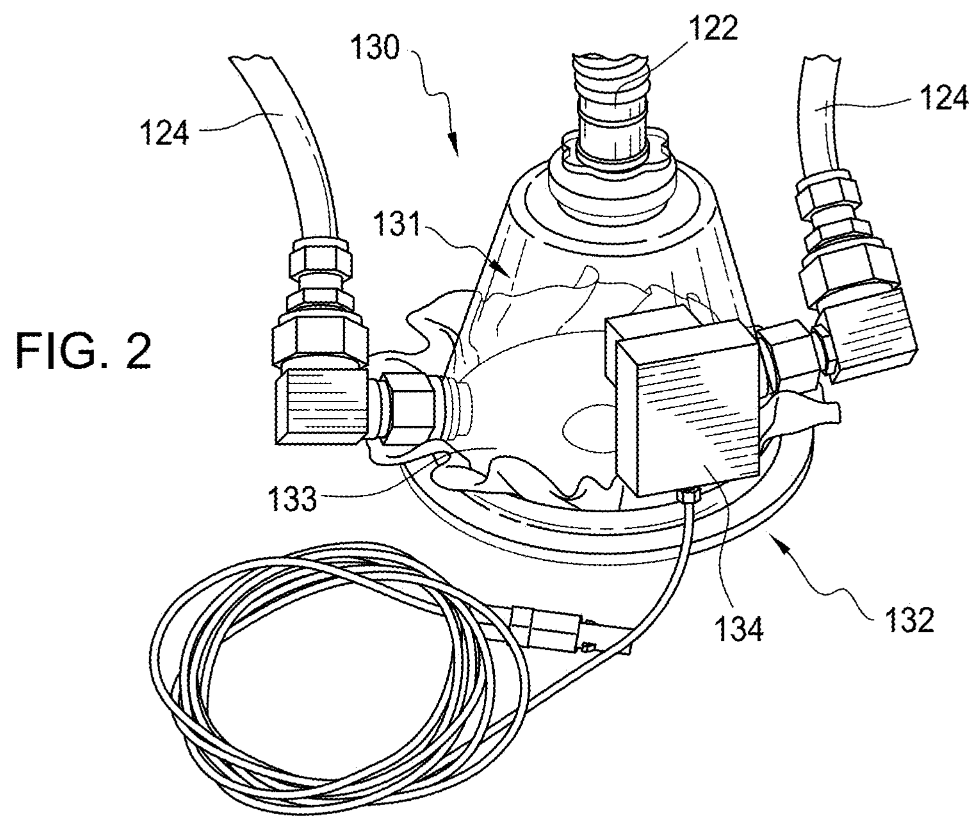
FIG. 2 illustrates an example of a challenge plethysmography mask according to at least one embodiment of the invention.
Figure 3:
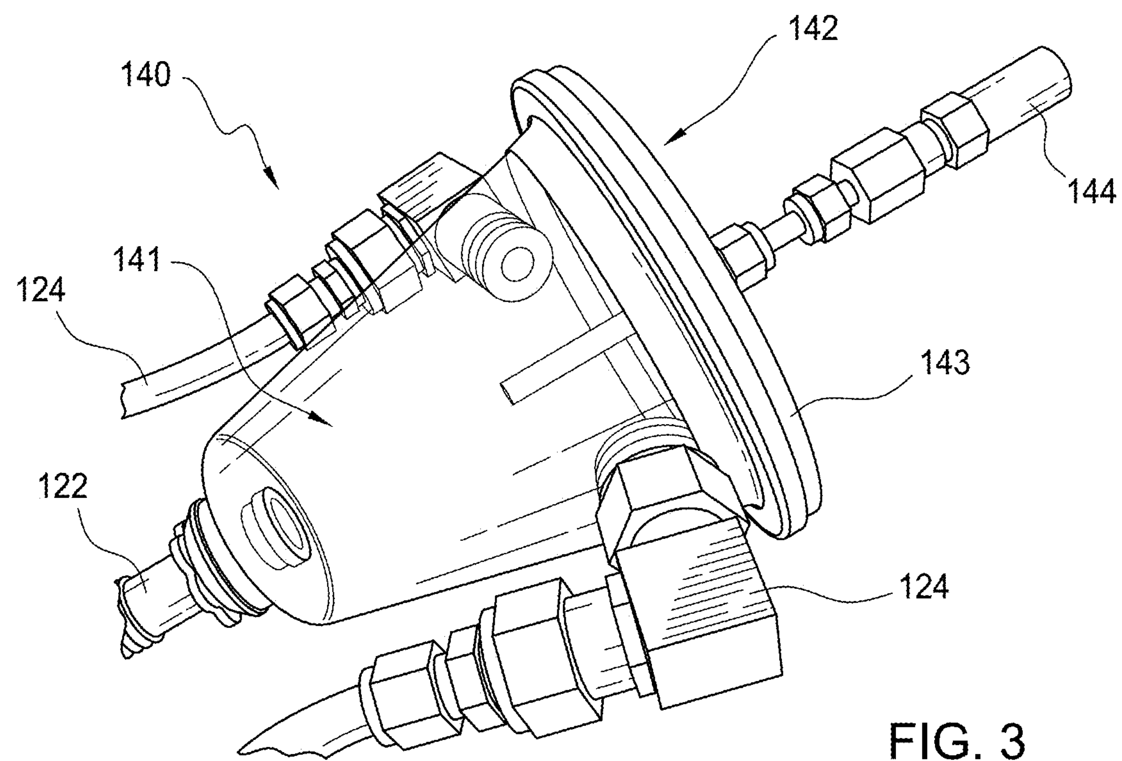
FIG. 3 illustrates an example of a sampling mask according to at least one embodiment of the invention.

120. The inhalation may take a variety of forms including, but not limited to, aerosol, gas, and vapor. The number of ports present in the plenum 120 dictates the number of challenge plethysmography masks 130, an example is illustrated in FIG. 2, and sampling masks 140, an example is illustrated in FIG. 3, that may attach to the plenum 120. In at least one embodiment, any unused ports in the plenum 120 are sealed with, for example, a cover. In at least one embodiment, each mask 130, 140 includes an input (e.g., a delivery conduit) and two outlets (e.g., exhaust conduits), which in at least one embodiment are on opposing surfaces of the mask, that are in fluid communication with a mask cavity 131, 141. In a further embodiment, the two outlets are joined together prior to connection with plenum 120 to reduce the number of ports used for each mask (e.g., two ports versus three ports), which leads to additional masks being able to be attached to a particular plenum. The at least one challenge mask 130 and the at least one sampling mask 140 are in fluid communication with the plenum 120. At least one sampling mask 140 allows for monitoring of at least one of particle size and aerosol concentration. Each challenge plethysmography mask 130 includes a pressure sensor in electrical communication with a processor 138 such as one present in a computer or other computing device to facilitate monitoring the pressure within the challenge mask cavity 131 during operation of the system. The plenum 120 is in fluid communication with an exhaust system 150 that facilitates the flow of the inhalation aerosol, gas, vapor through the plenum 120. The processor 138 based upon the pressure readings and readings from the at least one sampling mask 140 determines the amount of exposure to the inhalant by the test animal breathing in the aerosol, gas, vapor present in the challenge mask 130.

Figure 4:
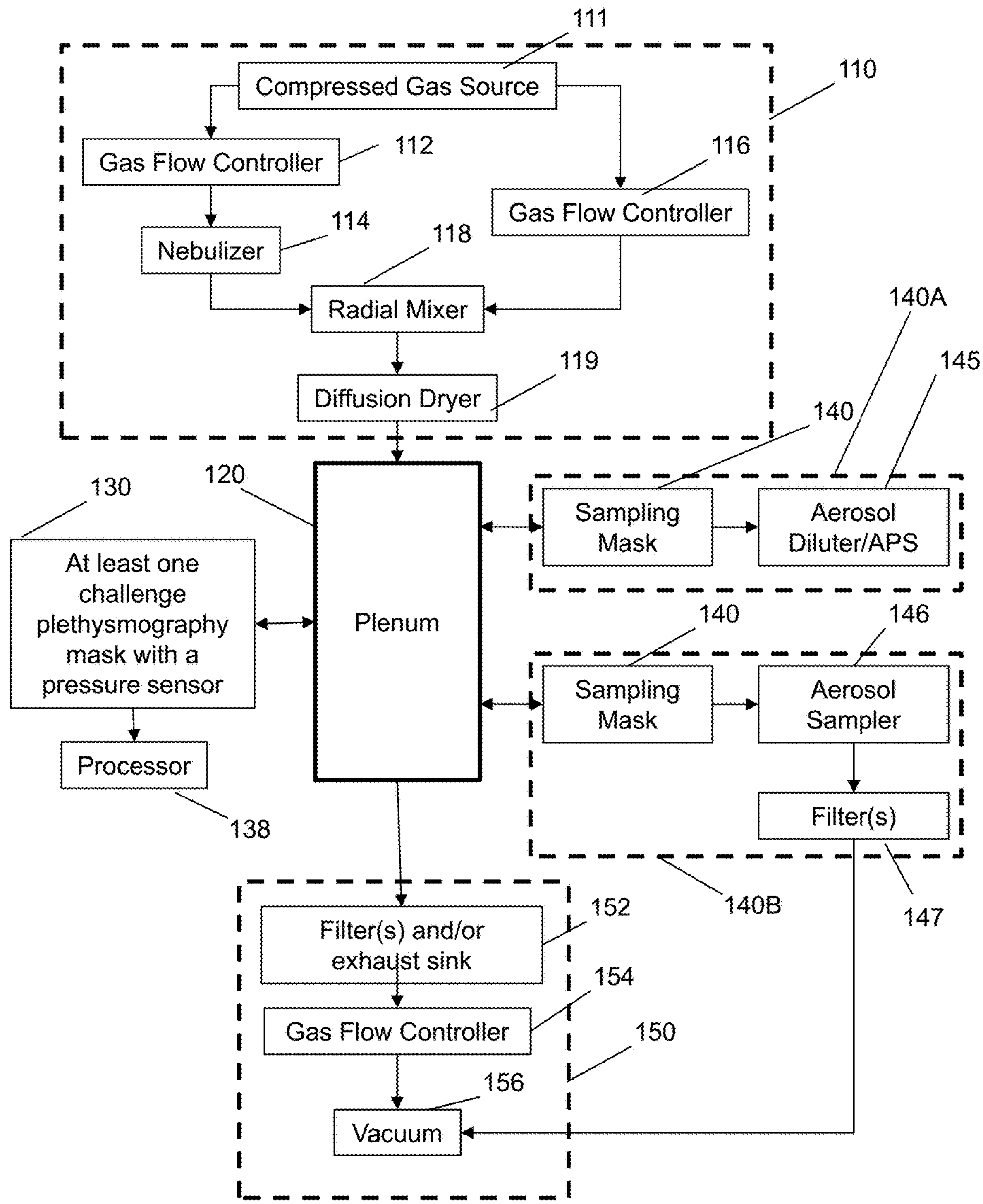
FIG. 4 illustrates a block diagram according to at least one embodiment of the invention.
Figure 5:
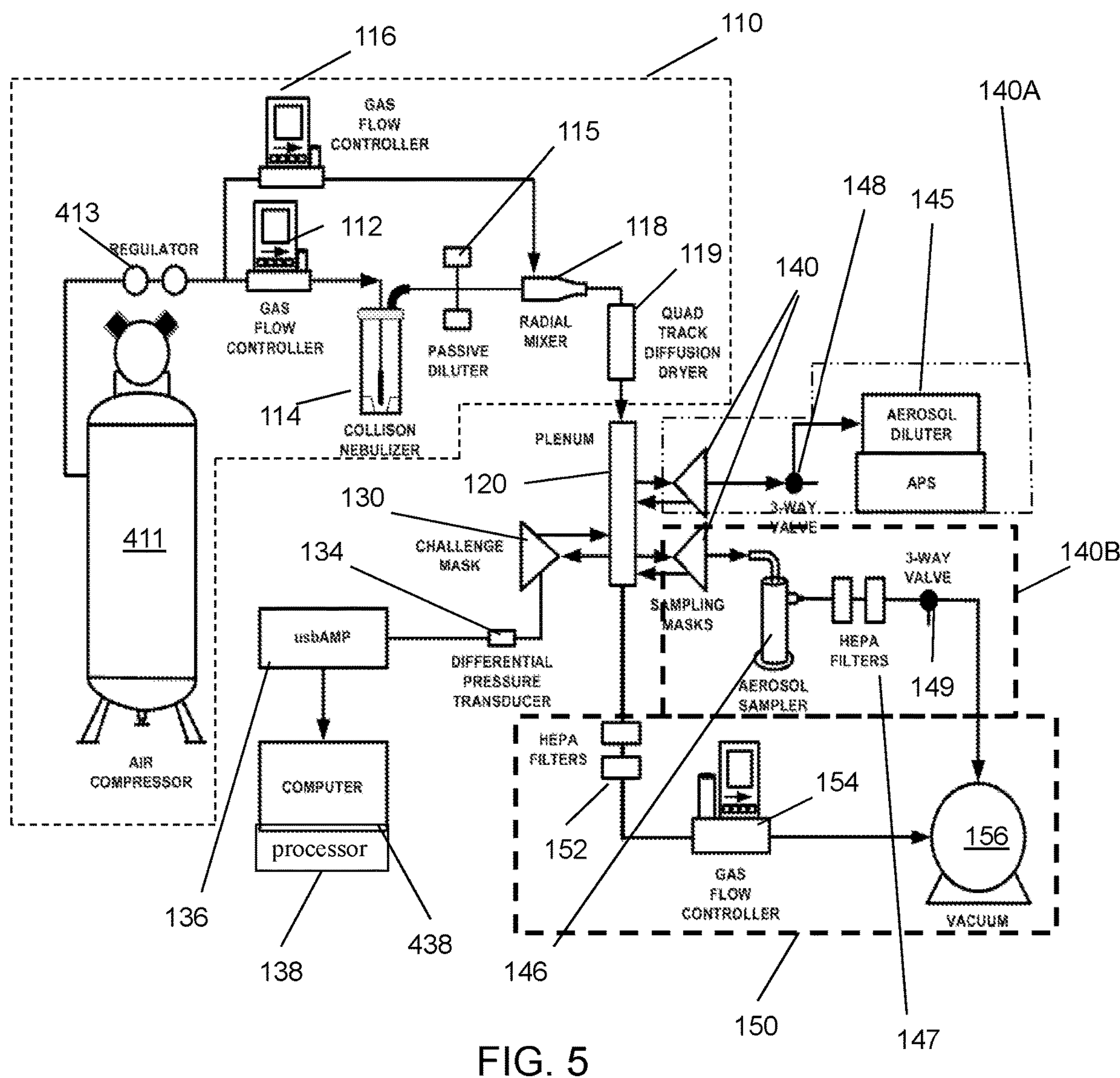
FIG. 5 illustrates a schematic according to at least one embodiment of the invention.

The inhalation source 110 and the exhaust system 150 may take a variety of forms other than that illustrated in FIGS. 4 and 5. The inhalation source 110 is representative of components that are capable of providing an aerosol, gas, or vapor to be used in exposing test animals attached to challenge masks 130. Examples of what may be present in the aerosol, gas or vapor includes, but not limited to, pharmaceuticals, biologicals, environmental toxins, and industrial chemicals. Material includes organic and inorganic compounds. Material in at least one embodiment is material that is not commonly found in the environment and it is desired to be used for an inhalation study. The exhaust system 150 is representative of components that are capable of providing an outlet for the flow of aerosol, gas, or vapor from the plenum 120. In at least one embodiment, any aerosol, gas, or vapor that is to exit the system passes through one or more filters to remove the inhalant material prior to exiting the system. In an alternative embodiment, the system further includes an exhaust sink having, for example, a chlorine bleach reservoir sufficient to kill/neutralize organic inhalants such as biological aerosols. In a further embodiment, the exhaust sink replaces one or more filters, for example as illustrated in FIG. 4.

Figure 6:
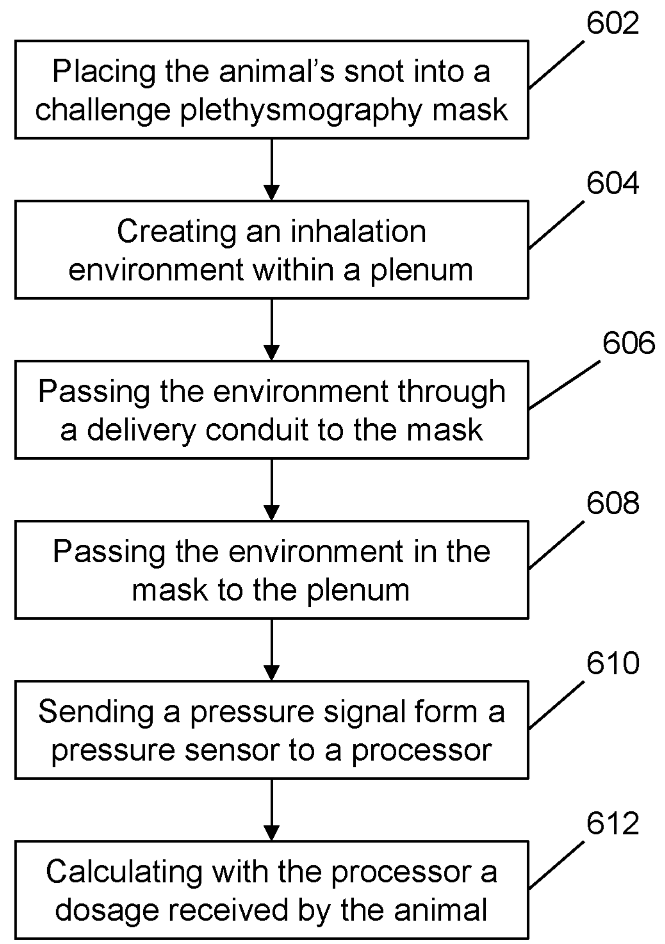
FIG. 6 illustrates a method according to at least one embodiment of the invention.

FIG. 2 illustrates an example of the challenge plethysmography mask 130 and FIG. 3 illustrates an example of the sampling mask 140 that may be used as part of the system illustrated in FIG. 1, 5, or 6. Both the challenge plethysmography mask 130 and the sampling mask 140 include an input conduit 122 that runs from a port in the plenum 120 to the mask and a pair of outlet (or exhaust) conduits 124 that are on opposing sides of the mask. In at least one embodiment, the outlet connections are connected with a T or Y connector prior to connection to a port in the plenum 120. In at least one embodiment, the two outlet conduits 124 are located on opposing surfaces of the mask to provide a balance exhaust draw relative to the input conduit 122, which in at least one embodiment is on an opposing end of the mask to the mask cavity opening 132, 142. In an alternative embodiment, there is just one exhaust conduit 124 per mask 130, 140. In other alternative embodiments, there are more than two exhaust conduits 124 for each mask.

The challenge plethysmography mask 130 illustrates a dental dam 133 over the opening end 132 of the mask to facilitate a seal around the animal's snout (e.g., nose and mouth) depending on the animal. Although in other embodiments, the dental dam 133 is omitted when for example the mask is sized for the animal being tested. The challenge plethysmography mask 130 further includes a pressure sensor 134 attached to the mask cone at, for example, a mid-point between the exhaust conduits 124 to provide a pressure reading of the mask cavity 131 that allows for measurement of the change in pressure resulting from the animal's respiratory activity. The pressure sensor 134 in at least one embodiment is attached to an amplifier (or other signal conditioner) 136 prior to being attached to the processor 138. Although in at least one embodiment, the amplifier is omitted.

The sampling mask 140 includes a sealing wall 143 over the opening 142 of the mask with a sampling conduit 144 passing therethrough. In at least one embodiment, the sampling conduit 144 is inserted into the mask 140 such that its sampling end samples near the center of the mask cavity 141. In at least one embodiment, the aerosol, gas, or vapor is drawn into the sampling conduit 144 with a vacuum to facilitate the collection of aerosol, gas, or vapor for characterization. An example of the sealing wall 143 is a piece of Plexiglas or other solid material fitted to the mask opening 142 and sealed in place to prevent leakage.

FIG. 4 illustrates a system according to at least one embodiment.

The inhalation source 110 is illustrated as including a compressed gas source 111 that is in fluid communication with a pair of gas flow controllers 112, 116. In at least one embodiment, the gas present in the compressed gas source 111 is a predetermined mixture substantially free of inhalant material beyond what is naturally found in the atmosphere. One gas flow controller 112 is in fluid communication with a nebulizer 114, although in at least one alternative embodiment the nebulizer 114 is replaced by other components that are capable of adding an inhalant material into the gas flow to create an aerosol. Examples of those other components include, but are not limited to, compressed gas cylinder, dry powder aerosol generator, nanoparticle generator, and vapor generator. The nebulizer 114 and the gas flow controller 116 are in fluid communication with a radial mixer 118 that is in fluid communication with a diffusion dryer 119, which is in fluid communication with the plenum 120. In an alternative embodiment, the second gas flow controller 116, the radial mixer 118 and/or the diffusion dryer 119 are omitted.

FIG. 4 illustrates two examples of sampling masks 140A, 140B attached to different components to measure different qualities and/or characteristics of the aerosol, gas, or vapor (i.e., the environment within the plenum 120). The sampling mask 140A is illustrated as being in fluid communication to an aerosol diluter and aerodynamic particle sizer (or APS) devices 145 that determine (or alternatively provides a signal representative of particle size) the size of the aerosol particles present in the aerosol present in the plenum 120. In at least one embodiment, the APS 145 is in electrical communication with the processor to provide an electrical signal representing its readings. The sampling mask 140B is illustrated as being in fluid communication to an aerosol sampler 146 to provide a reading as to the concentration of the aerosol present in the system. The aerosol sampler 146 is in fluid communication with a filter(s) 147 that remove a fraction of the aerosol from the gas flow prior to routing the gas flow to a vacuum 156. In an alternative embodiment, there is a sampling mask attached to a particle counter, which in a further embodiment is in electrical communication with the processor 138.

The illustrated exhaust system 150 in FIG. 4 includes a filter(s) 152 in fluid communication with a gas flow controller 154, which is in fluid communication with a vacuum 156. The vacuum 156 establishes a flow of aerosol gas from the plenum 120 into the exhaust system 150 and in at least one embodiment into the sampling mask 140B and associated components. As mentioned previously, the filters 147, 152 are present to remove the aerosol material from the gas flow prior to exhausting the gas flow to a different environment or further processing/cleaning prior to eventual release to the atmosphere. An example of the filters 147, 152 is HEPA filters. The exhaust system 150 may take a variety of other configurations while still providing in at least one embodiment a negative pressure draw on the plenum 120.

In at least one embodiment, the gas flow controllers provide regulation for the flow of gas through the inhalation source 110 and the exhaust system 150 and as such also through the plenum 120 and the masks 140, 150. In at least one embodiment, there are a variety of parameters that can be detected by sensors that may control or at least impact operation of the gas flow controllers including, but not limited to, aerosol concentration, aerosol particle size, temperature, pressure, humidity, air flow rate including refreshing the contents of the plenum, etc.

FIG. 5 illustrates a further embodiment according to the invention. The compressed gas source 111 is illustrated as an air compressor 411 that is in fluid communication with a regulator 412, which in at least one embodiment is controlled by at least one controller such as the gas flow controllers 112, 116 or other computer based controller. The nebulizer 114 is illustrated as a collision nebulizer that is in fluid communication with a passive diluter 115 prior to connection with the radial mixer 118. The diffusion dryer 119 is illustrated as being a quad track diffusion dryer. Also illustrated in FIG. 5 is a pair of alternative embodiments represented by valves 148, 149, which in at least one embodiment are 3-way valves. The valves allows for the APS 145 and/or the aerosol sampler 146 to be sample continuously or intermittently.

The challenge mask 130 is illustrated as having a differential pressure transducer 134 (as the pressure sensor) that is in electrical communication with an amplifier 136, which in at least one embodiment would have an output capable of attachment to a computer such as an USB connector. The processor 138 is illustrated as being part of a computer 438, which is in electrical communication with the amplifier 136, which as discussed previously may be omitted in at least one embodiment. In at least one embodiment, the computer 438 is in electrical communication with the APS 145 to be able to characterize the aerosol present in the plenum 120. The characterization of the aerosol when combined with the respiratory information for the test animal provides exposure information, which allows for determination of dosimetry for the test animal to the material present in the aerosol gas.

In at least one embodiment, the signal provided by the pressure sensor 134 to the computer 438 provides respiratory frequency and tidal volume. The respiratory frequency when combined with the tidal volume provides a minute volume. In at least one embodiment, the computer 438 correlates the characterization data for the aerosol gas with the respiratory information to determine the exposure information and thus the exposure level by the minute. In an alternative embodiment, different time lengths (or epochs) are used. Examples of different time lengths for determining exposure level include, but are not limited to, 1 minute, 2 minutes, 5 minutes, 10 minutes, and 20 minutes. In a further alternative embodiment, the exposure time is determined based on when the animal inhales the target dosage.

FIG. 6 illustrates a method according to at least one embodiment of the invention. Based on this disclosure, one of ordinary skill in the art should appreciate that multiple animals may be exposed at substantially the same time with the processor handling multiple signal feeds. In at least one embodiment, the length of the exposure is determined based upon the dosage level. As illustrated in FIG. 6, the method begins with placing the animal's snout into a challenge plethysmography mask, 602. An inhalation environment is created within a plenum, 604. Examples of the ways to do this are using the variety of approaches discussed above in connection with FIGS. 1, 4, and 5. The environment is passed through a delivery conduit to the mask on the animal's snout, 606. As referenced previously, multiple masks may be supplied the environment in the plenum. The environment in the mask is passed to the plenum through the exhaust conduit(s), 608. A pressure sensor on the mask sends a pressure signal to the a processor, 610. The processor calculates a dosage received by the animal wearing the particular mask, 612.

To test the accuracy and ability of the system to perform, an aqueous 25 mg/mL saline solution compounded using 53014 bulk NaCl (Sigma-Aldrich, St. Louis, Mo.) and model W9-1 Ultra Trace Elemental Analysis Water (Fisher Scientific, Hanover Park, Ill.) was used to determine time-to-99% steady state aerosol concentration ($T_{99}$), system aerosol concentration homogeneity (spatial distribution) and particle size distribution. To confirm use of a pressure signal collected from a ventilated challenge plethysmography mask and to be integrated into a respiratory waveform, a certified calibrated model CR1311 100 $cm^3$ gas tight syringe (Hans Rudolph, Inc., Shawnee, Kans.) was used. The syringe was connected to the sealed end of the mask using a Luer-lock fitting such as may be present on a sampling mask. The mask aerosol delivery and exhaust conduits were connected to a 12-port plenum. The challenge plethysmography mask was ventilated at a volumetric flow rate of 4.0 L/min and a pressure of −0.4 inches water column. For calibration, a 20 $cm^3$ bolus of air was injected into the mask and the resulting impulse response from the pressure transducer was captured and processed by IOX Software. To simulate tidal breathing, 20, 40, and 60 $cm^3$ (nominal) volumes of air were cyclically injected into and withdrawn from the mask. Respiratory waveforms were recorded and frequency, tidal volume and minute volume were determined.

To demonstrate that respiratory waveforms could be collected from a ventilated challenge plethysmography mask in the presence of an aerosol, the 12-port plenum was set up with a single challenge plethysmography mask and two sample collection masks. For this test, the challenge plethysmography and sample collection masks were each ventilated at a flow rate of 5.0 L/min. The radial mixer was set at a flow rate of 5.0 L/min. A Model 3321 APS and Model 3302A Aerosol Diluter operating at 5.0 L/min. were configured in series and connected to one sample collection mask. A 25 mm filter holder was connected to the second sample collection mask and operated at 2.0 L/min. A 25 mg/mL saline solution was used to produce the test aerosol. Tidal breathing was simulated by injecting and withdrawing 40 $cm^3$ (nominal) boluses of air. Respiratory waveforms were recorded and frequency, tidal volume and minute volume were determined.

Figure 7:
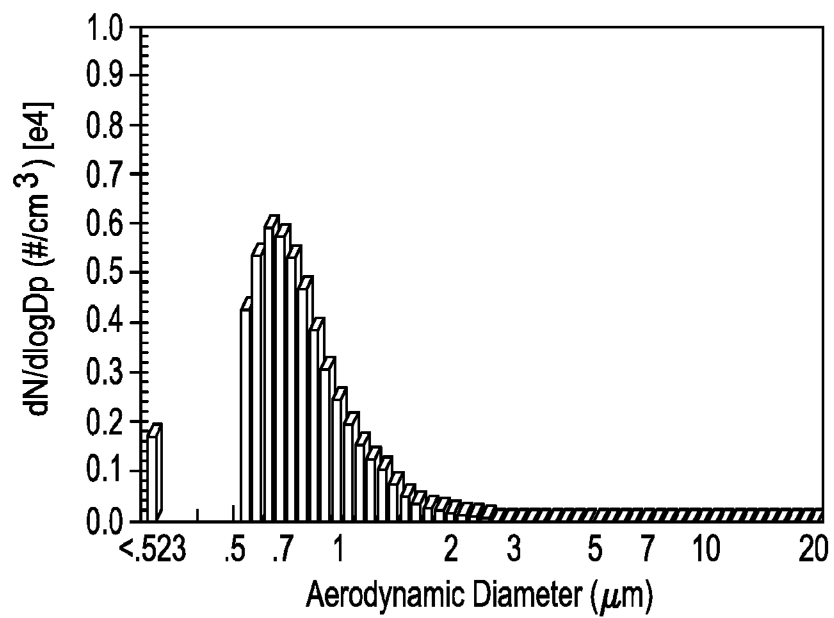
FIG. 7 illustrates an experimental 25 mg/mL NaCl count particle size distribution.

FIG. 7 illustrates the 25 mg/mL NaCl count particle size distribution. The CMAD equaled 0.7 μm (micrometer) and GSD equaled 1.3. Approximately 83% of the number of saline particles was less than 1 μm (micrometer) and 99.9% were less than 3 μm (micrometer). The dN/dlogDp was the differential count normalized to total count within a specified particle size range.

Figure 8:
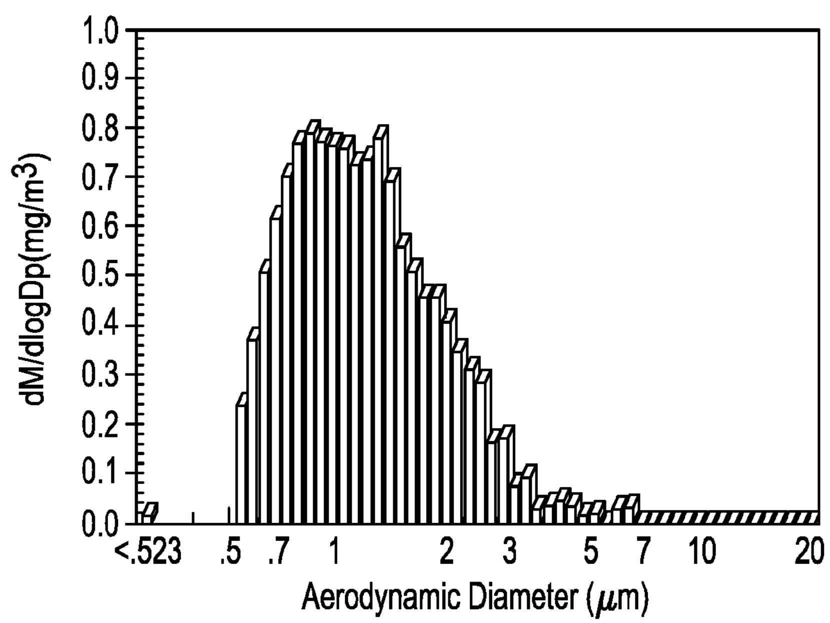
FIG. 8 illustrates an experimental 25 mg/mL NaCl mass particle size distribution.

FIG. 8 illustrates the 25 mg/mL NaCl mass particle size distribution. The MMAD equaled 1.2 μm (micrometer) and GSD equaled 1.7. Approximately 42% of the mass of saline particles was less than 1 μm (micrometer) and 97% was less than 3 μm (micrometer). The dM/dlogDp was the differential mass normalized to total mass within a specified particle size range.

Figure 9:
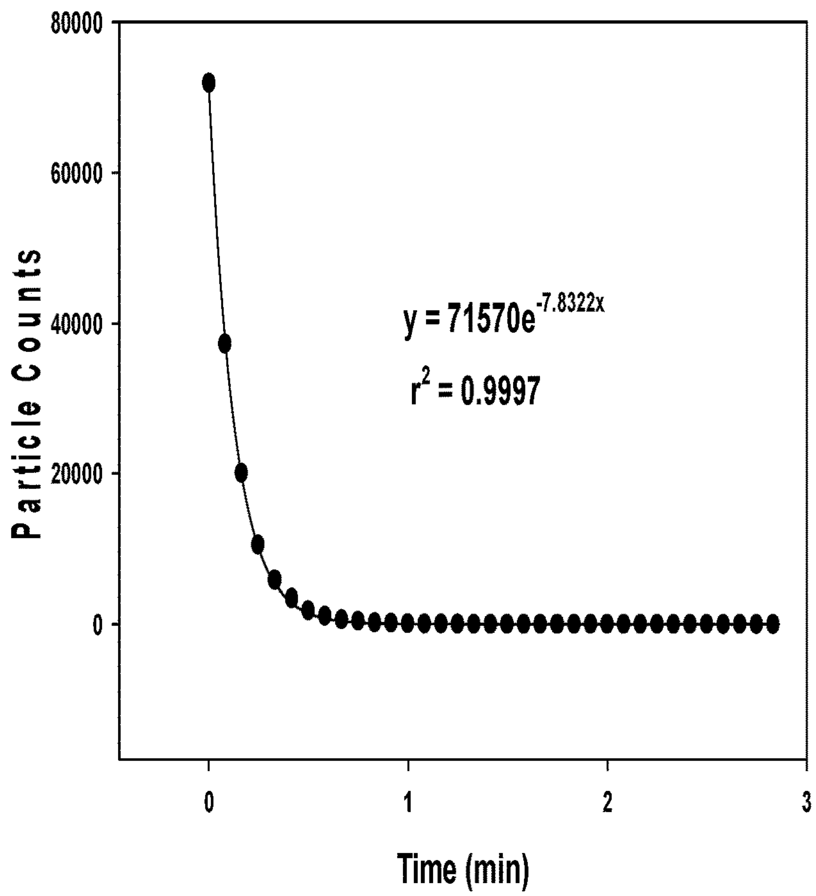
FIG. 9 illustrates a $T_{99}$ determination for experimental data illustrated in FIGS. 6 and 7.

FIG. 9 illustrates the $T_{99}$ determination. The time versus particle count "fingerprint" of a saline aerosol data was plotted as illustrated in FIG. 9. The decay section of the curve was identified and isolated. A SigmaPlot table was created in which the initial value was the point in the decay curve with the most particle counts and the time was set at 0 (zero) minutes. Additional decay curve data were added to the table and the time was incremented by five seconds. Data points continued to be added until the particle count was less than 10. The resulting table was plotted and fitted with the exponential decay, single, 2 parameter equation:

$$y=ae^{-kt}$$

where k is a rate of change constant and t is time.

The observed $T_{99}$ is given by the equation:

$$T_{99}=\ln 100\times\frac{1}{7.8322}=0.588\text{ min}$$

Spatial variation of aerosol from a 25 mg/mL saline solution in the oro-nasal inhalation plethysmography mask exposure system was calculated using filter samples. The mean filter sampler volumetric flow rate for the filter sampler during the temporal variation tests was 2.193 L/min. The sample collection time was 30 minutes and the volume of aerosol sampled was 65.79 L. The mean aerosol concentration=0.1203±0.0006 mg/L (n=3) and the % CV was 0.51. For total variation tests, the mean filter sampler volumetric flow rate was 2.150±0.010 L/min. The sample collection time was 30 minutes and the mean volume of aerosol sampled was 64.49 L. The mean aerosol concentration=0.0981±0.0011 mg/L (n=3) and the % CV was 1.1. Spatial variation was 0.9%, as calculated from the following equation:

$$CV_{spatial}^2(\%)=CV_{total}^2(\%)CV_{temporal}^2(\%)$$

Figure 10:
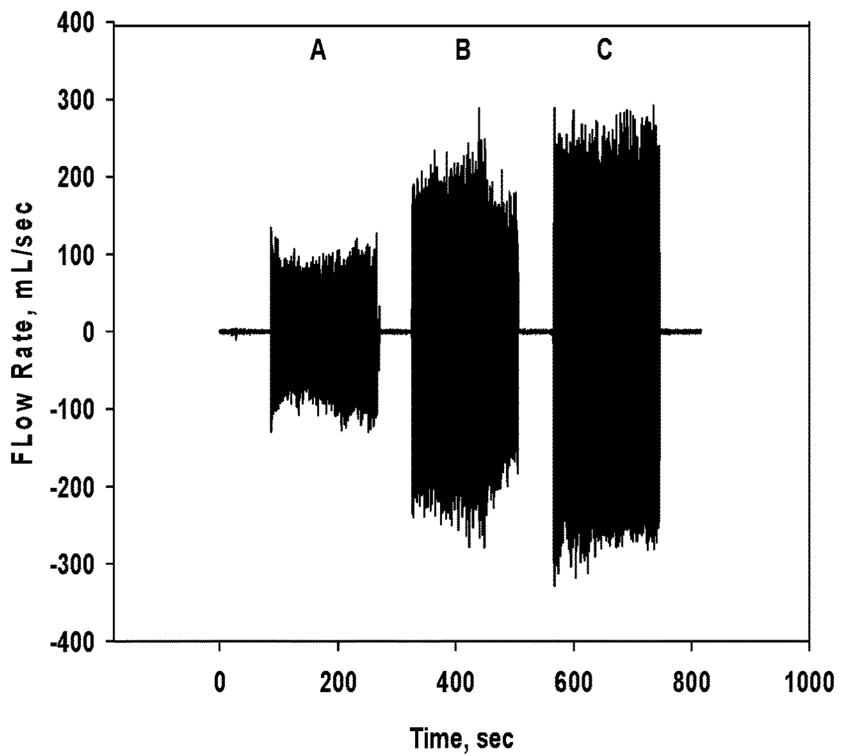
FIG. 10 illustrates simulated respiratory waveforms that were obtained using a syringe during an experiment.

FIG. 10 illustrates the simulated respiratory waveforms that were obtained using the syringe. The following tables illustrate the data that was collected for the simulated tidal breathing: 20 mL, 40 mL, and 60 mL.

TABLE A

| | |
|---|---|
| Mean Tidal Volume = | 21.0 ± 1.3 $cm^3$ |
| Mean Frequency = | 62 ± 5 breaths/min |
| Mean Minute Volume = | 1289 ± 97 L/min |

TABLE B

| | |
|---|---|
| Mean Tidal Volume = | 41.9 ± 1.5 $cm^3$ |
| Mean Frequency = | 69 ± 6 breaths/min |
| Mean Minute Volume = | 2909 ± 317 L/min |

TABLE C

| | |
|---|---|
| Mean Tidal Volume = | 60.7 ± 1.3 $cm^3$ |
| Mean Frequency = | 62 ± 2 breaths/min |
| Mean Minute Volume = | 3784 ± 136 L/min |

Simulated respiratory waveforms from the ventilated challenge-plethysmography mask were collected under two environments: no aerosol and aerosol present. The aerosolize 25 mg/mL saline solution flowed into the inhalation plethysmography mask. The simulated respiratory waveforms from the challenge-plethysmography mask in the presence of aerosol were obtained. Data for a simulated tidal breathing of 40 mL is present below in Tables D (no aerosol) and E (aerosol). The percent difference between no aerosol and aerosol is provided in Table F.

TABLE D

| | |
|---|---|
| Mean Tidal Volume | 40.6 ± 0.8 $cm^3$/min |
| Mean Frequency | 80 ± 9 breaths/min |
| Mean Minute Volume | 3237 ± 317 $cm^3$ |

TABLE E

| | |
|---|---|
| Mean Tidal Volume | 40.4 ± 1.3 $cm^3$/min |
| Mean Frequency | 84 ± 8 breaths/min |
| Mean Minute Volume | 3373 ± 255 $cm^3$ |

TABLE F

| | |
|---|---|
| Mean Tidal Volume | 0.5% |
| Mean Frequency | 4.9% |
| Mean Minute Volume | 4.1% |

Next, accuracy of the respiratory parameters collected from the challenge plethysmography mask using live animals was evaluated in direct comparison tests with nonhuman primate and rabbit head-out plethysmographs. For nonhuman primates, a Model PLT_SC_PM cylindrical Plexiglas plethysmograph (emka Technologies, Falls Church, Va.) was used. The cylindrical plethysmograph, with an internal volume of 34.9 L, was leak tested as previously described (Mokler & White, 1983). Nonhuman primates were sedated with TELAZOL® anesthetic (Lot #SEM040115-1, Zoetis Services, LLC, Florham Park, N.J.) and placed in the head-out plethysmograph in a dorsal recumbent position. The head of the animal was gently pushed through an annular orifice in an 8 mil sheet of rubber dam material that sealed around its neck. After closing the cylindrical plethysmograph, the challenge-plethysmography mask was placed over the snout of the nonhuman primate. For the rabbits, a custom rectangular Plexiglas plethysmograph was used. Alert rabbits were placed in cat-sack restraints (Four Flags Over Aspen, Inc., St. Clair, Minn.) and placed inside the plethysmograph in a supine position. Similarly, a dental dam collar was placed around the neck. Respiratory parameters were recorded simultaneously from the challenge plethysmography mask and head-out plethysmographs for subsequent analysis.

Figure 11:
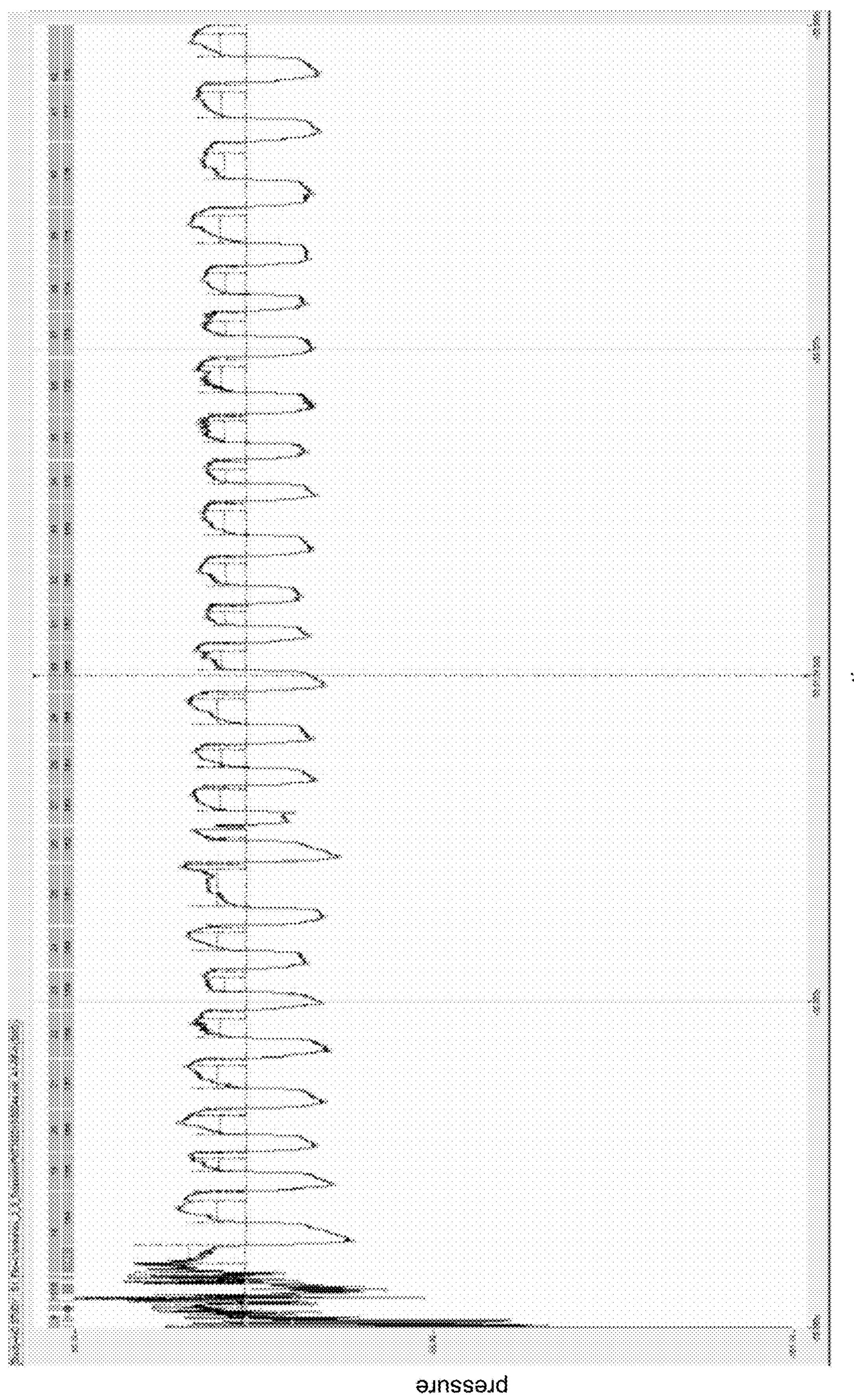
FIG. 11 depicts a plethysmography graph for a non-human primate wearing a challenge plethysmography mask similar to that illustrated in FIG. 2.
Figure 12:
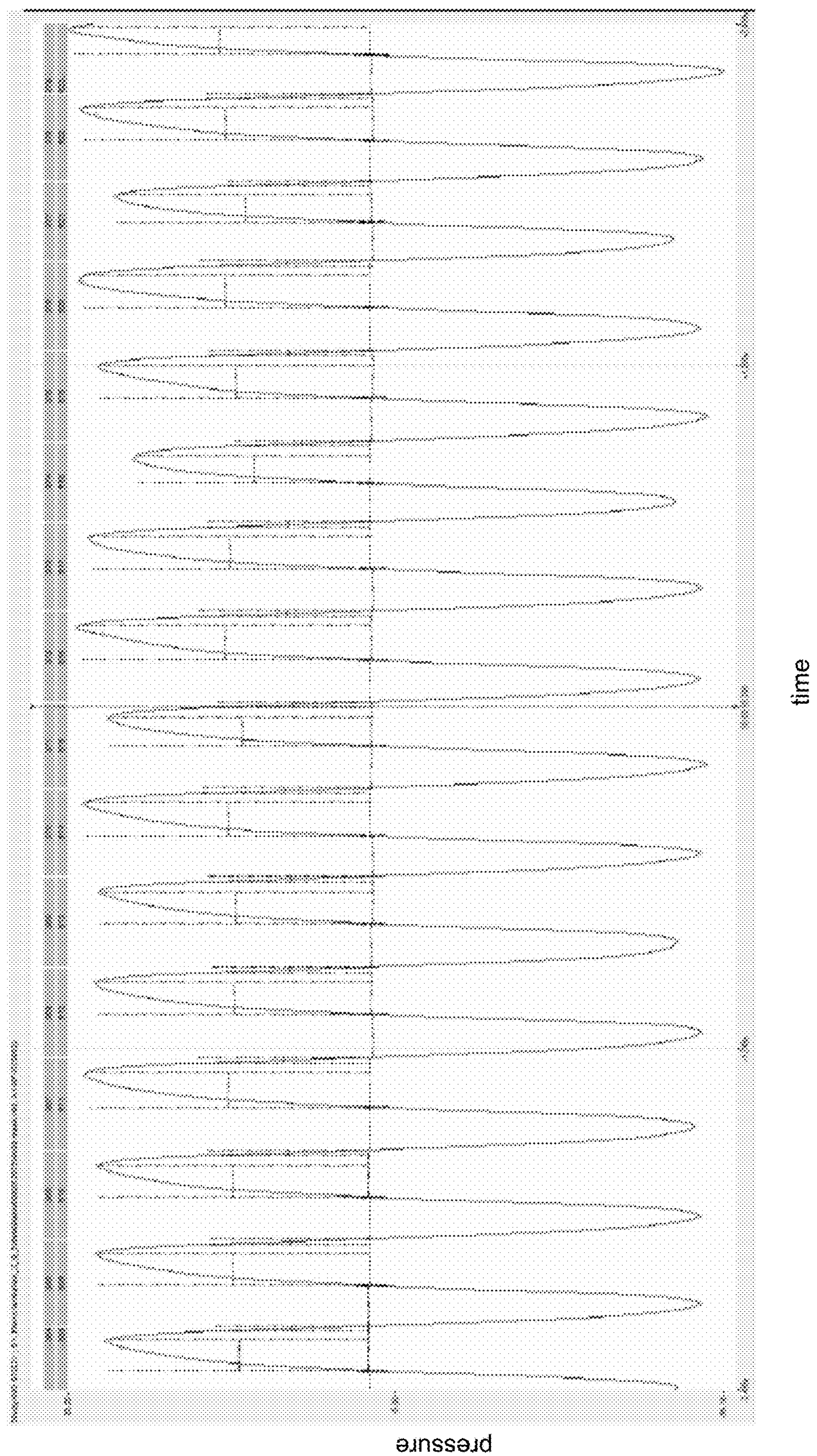
FIG. 12 depicts a plethysmography graph for a rabbit wearing a challenge plethysmography mask similar to that illustrated in FIG. 2.

FIGS. 11 and 12 depict pressure readings representing respiratory activity of a test animal (nonhuman primate and rabbit, respectively). The pressure readings were obtained from the pressure sensor on the challenge plethysmography mask illustrated in FIG. 2 used in the system illustrated in FIG. 5.

The nonhuman primate exposure (using three test animals) provided the following respiratory data, tidal volume, frequency, and minute volume present in Table G—Head-Out Plethysmograph, Table H—Challenge Plethysmography Mask, and Table I—the differences between the measurements.

TABLE G

| ID | TV ($cm^3$) | f bpm | MV ($cm^3$/min) |
|---|---|---|---|
| 0028 | 19.0 | 32.8 | 452.8 |
| 8804 | 33.8 | 14.1 | 479.0 |
| 779880 | 21.6 | 25.8 | 557.3 |

TABLE H

| ID | TV ($cm^3$) | f bpm | MV ($cm^3$/min) |
|---|---|---|---|
| 0028 | 13.8 | 50.2 | 365.1 |
| 8804 | 27.0 | 15.9 | 552.4 |
| 779880 | 18.4 | 32.5 | 597.7 |

TABLE I

| ID | TV ($cm^3$) | F bpm | MV ($cm^3$/min) |
|---|---|---|---|
| 0028 | 5.20 | 17.4 | 87.7 |
| 8804 | 6.80 | 1.8 | 73.4 |
| 779880 | 3.20 | 6.7 | 40.4 |

The New Zealand White rabbit exposure (using three test animals) provided following respiratory data, tidal volume, frequency, and minute volume present in Table J—Head-Out Plethysmograph, Table K—Challenge Plethysmography Mask, and Table L—the differences between the measurements.

TABLE J

| ID | TV ($cm^3$) | f bpm | MV ($cm^3$/min) |
|---|---|---|---|
| 377C | 10.4 | 200 | 2054 |
| 4B08 | 11.6 | 189 | 2150 |
| 5 | 27.2 | 157 | 4183 |

TABLE K

| ID | TV ($cm^3$) | f bpm | MV ($cm^3$/min) |
|---|---|---|---|
| 377C | 11.0 | 199 | 2158 |
| 4B08 | 9.9 | 190 | 1828 |
| 5 | 26.1 | 156 | 3982 |

TABLE L

| ID | TV ($cm^3$) | f bpm | MV ($cm^3$/min) |
|---|---|---|---|
| 377C | 0.6 | 1 | 104 |
| 4B08 | 1.7 | 1 | 322 |
| 5 | 1.1 | 1 | 201 |

The system built according to at least one embodiment of the invention was successfully demonstrated as being in compliance with standard aerosol and inhalation tests $T_{99}$, aerosol spatial distribution, and particle size distribution based on the data shown and discussed above. This system determined pulmonary parameters in real time during inhalation challenge using a volume displacement method thus eliminating head-out plethysmographs. In at least one embodiment, multiple animals may be challenged simultaneously while the challenge plethysmography mask reduces dermal exposure and eliminates ocular exposure.

At least one embodiment of the invention provides an Integrated Modular Bioaerosol Respiratory Exposure System (IMBRE) that includes a pneumatic/electronic control box and accompanying control computer program instructions that can utilize existing aerosol exposure chambers (e.g., commercial off the shelf (COTS) nose-only exposure chambers). The IMBRE (also referred to herein as the "system") can interface with particle sizing and counting devices that provide data streams to the computer program instructions, which can enable the control of exposure duration based on aerosol particle count (which can be correlated with presented dose).

The system can integrate real-time plethysmography (greater accuracy for calculating presented dose) via an isochoric chamber volume displacement method, which may not require calibration with each animal prior to use. More specifically, an isochoric mask can be placed over the snout (mouth and nares) of an animal; and, the mask can be ventilated with a test/challenge article suspended in breathing quality air (aerosol). The mask can be fitted with a differential pressure transmitter (DPT) connected to a signal amplifier, wherein the signal amplifier can be connected to a computing device with specialized plethysmography computer program instructions. As the animal breathes, positive and negative (relative) pressure pulses in the mask can be detected by the DPT, amplified, and reduced to a tidal volume and frequency by the plethysmography computer program instructions. The respiratory minute volume can be calculated as a product of tidal volume and frequency; and, a cumulative inspired volume can be calculated as the product of respiratory minute volume and exposure duration. The cumulative inspired volume can be integrated with the theoretical aerosol concentration to calculate the desired (target) inhaled volume of aerosol.

Additionally, the system can count aerosol particles and correlate particle counts with presented dose and determine particle size distribution. This feature can be used to determine the time required for "dose-calculated" exposures.

More specifically, aerosol particles can be diluted and collected from one sample collection mask using an in-line aerosol particle counter. Aerosol particles can be collected from a second sample collection mask using filters and liquid impingers. Samples from each mask can be collected over different lengths of time. The filter samples can be weighed and a mass per unit volume aerosol concentration calculated. The liquid impinger samples can be microbiologically assayed and a count per unit volume aerosol concentration can be calculated. The mass and count per unit volume aerosol concentrations can be plotted against the count data from the in-line particle counter and a mathematical regression correlation can be determined. The mathematical correlation can be used to determine dosimetry of subsequent exposures.

At least one embodiment of the invention provides a compact and modular system that runs aerosol exposures using a nose-only chamber, a head-only exposure chamber, or a whole-body exposure chamber. At least one embodiment of the invention uses a mask system where the system performs real-time plethysmography (greater accuracy for calculating the presented dose). The system can expose animal experimental models to biological, chemical, and radiological agents for pathogenesis and/or toxicity studies for therapeutic, vaccine, and/or prophylactic development. The system can also be used to test aerosolized drug formulations in animal models to facilitate the development of inhalable drugs within the pharmaceutical industry.

In at least one embodiment, the system provides improved spray accuracy, including integrated real-time plethysmography, particle-based tracking of concentration (oronasal mask module), real-time adjustment of exposure time, and/or continuous spray improvement based on previous run data across all systems (animal, agent, agent media, etc.). The system may also provide spray analysis and reporting, integrated calibration of all components, and/or system health detection and analysis. Specifically, the system may detect the likelihood of component failure before any run and ensure that all components and/or accessories are in calibration before each spray, where component heath and calibration can be transferable to other systems.

FIG. 13 is a flow diagram illustrating a method for controlling aerosol respiratory exposure according to an embodiment of the invention. A differential pressure transmitter in a respiratory exposure mask can detect positive pressure pulses and negative pressure pulses in the respiratory exposure mask 1310. Specifically, a differential pressure transducer can generate a pressure differential waveform and transmit the pressure differential waveform to a processor for further calculation.

Plethysmography software in the processor can determine tidal volume and frequency based on the detected positive and negative pressure pulses 1320. The processor can also calculate the respiratory minute volume 1330, which may be a product of the tidal volume and the frequency. In at least one embodiment, the respiratory minute volume is an average integral over a respiratory waveform, where the respiratory waveform is measured, integrated over time, and averaged.

The processor can calculate the cumulative inspired volume 1340, which may be a product of the respiratory minute volume and an exposure duration. The cumulative inspired volume can be calculated by integrating the respiratory waveform over time in real-time until the desired presented dose is achieved. The processor can also calculate the desired inhaled volume of aerosol with the cumulative inspired volume and the theoretical aerosol concentration 1350. The total presented dose can be an integral of the product of a concentration function and a volume function over time when aerosol concentration changes over time.

Figure 14:
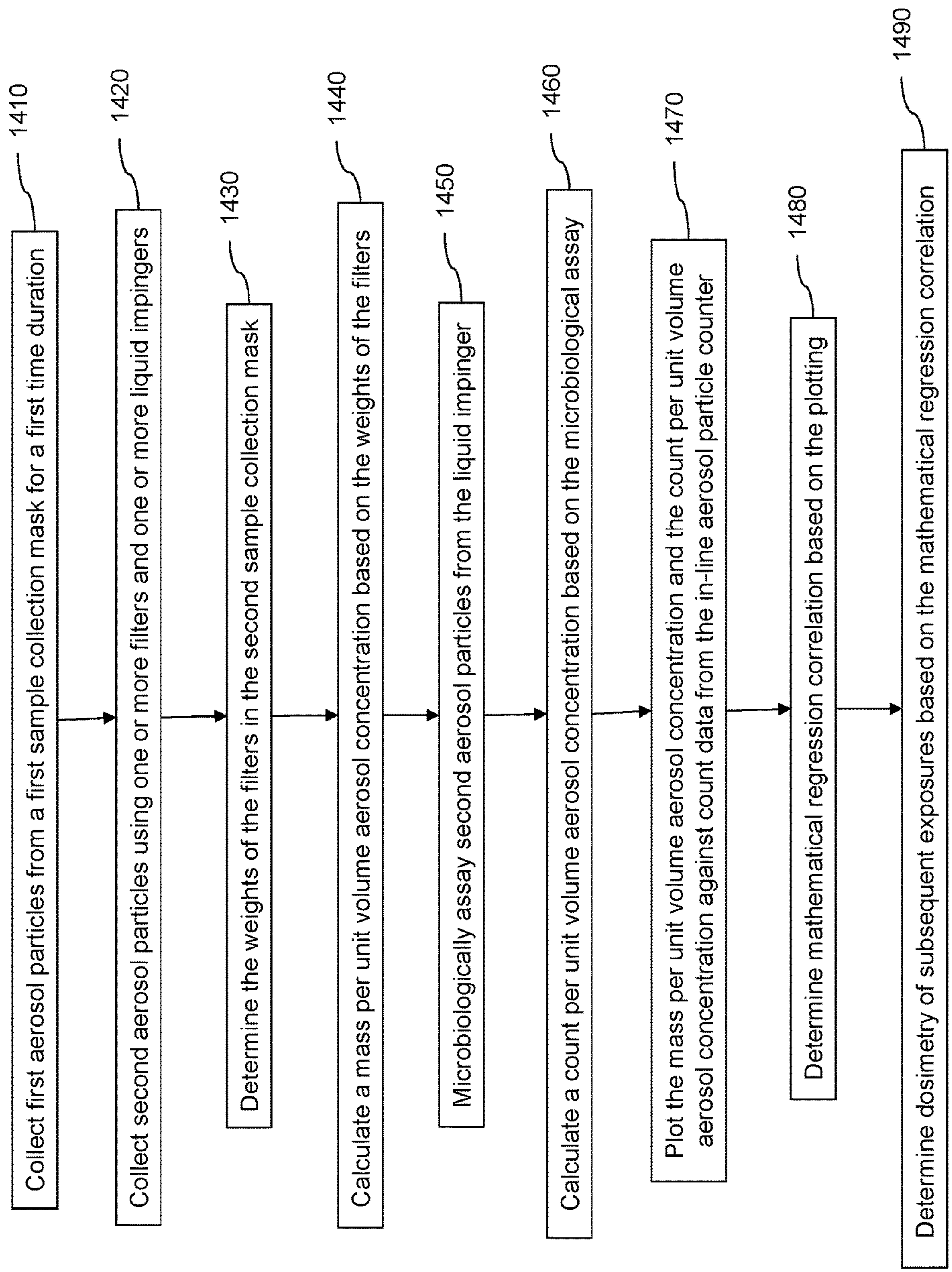
FIG. 14 is a flow diagram illustrating a method for controlling aerosol respiratory exposure according to an embodiment of the invention.

FIG. 14 is a flow diagram illustrating a method for controlling aerosol respiratory exposure according to an embodiment of the invention. The method can also determine aerosol particle size distribution (mass median aerodynamic diameter (μm (micrometer))) and geometric standard deviation or particle counts. An in-line aerosol particle counter can collect first aerosol particles from a first sample collection mask for a first time duration 1410. A second sample collection mask can collect second aerosol particles using one or more filters and one or more liquid impingers 1420. The second aerosol particles can be collected for a second time duration that is different from the first time duration.

In at least one embodiment, the weights of the filters in the second sample collection mask is determined 1430; and, a mass per unit volume aerosol concentration is calculated based on the weights of the filters 1440. Second aerosol particles from the liquid impinger can be microbiologically assayed 1450; and, a count per unit volume aerosol concentration can be calculated based on the microbiological assay 1460.

The mass per unit volume aerosol concentration and the count per unit volume aerosol concentration can be plotted against count data from the in-line aerosol particle counter to correlate a presented dose with the particle count 1470. A mathematical regression correlation can be determined based on the plotting of the mass per unit volume aerosol concentration and the count per unit volume aerosol concentration against the count data from the in-line aerosol particle counter 1480. Dosimetry of subsequent exposures can be determined based on the mathematical regression correlation 1490.

As will be appreciated by one skilled in the art based on this disclosure, aspects of the present invention may be embodied as a system, method or computer program product. Accordingly, aspects of the present invention may take the form of an entirely hardware embodiment, a processor operating with software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this disclosure, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Computer program code for carrying out operations for aspects of the present invention may be written in any combination of one or more programming languages, including an object oriented programming language such as Java, Smalltalk, C++, C#, Transact-SQL, XML, or the like and conventional procedural programming languages, such as the "C" programming language or similar programming languages. The program code may execute entirely on the user's computer, partly on the user's computer, as a standalone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute with the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 15:
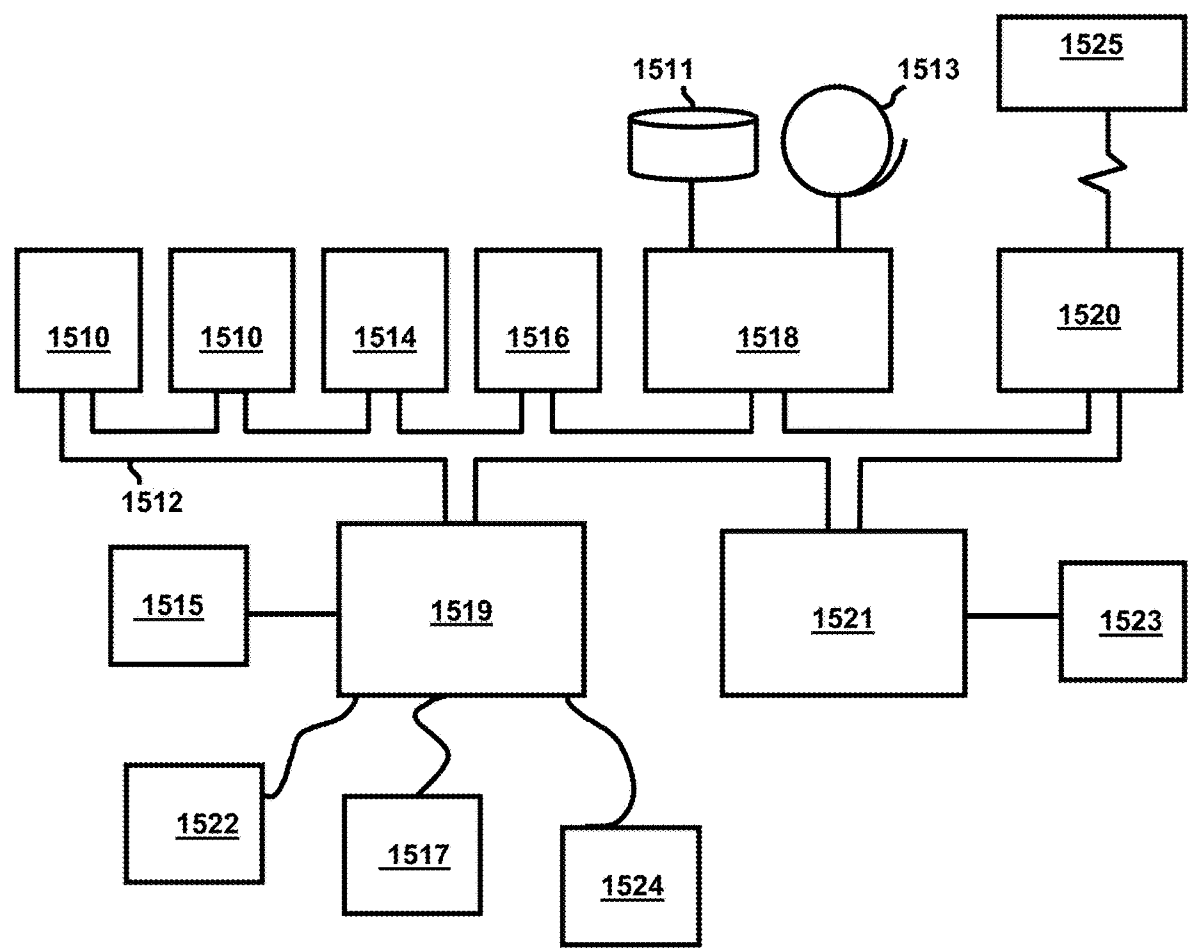
FIG. 15 illustrates a computer program product and computer implementation according to an embodiment of the invention.

Referring now to FIG. 15, a representative a hardware environment for practicing at least the first embodiment of the invention is depicted. This schematic drawing illustrates a hardware configuration of an information handling/computer system in accordance with at least one embodiment of the invention. The system comprises at least one processor or central processing unit (CPU) 1510. The CPUs 1510 are interconnected with system bus 1512 to various devices such as a random access memory (RAM) 1514, read-only memory (ROM) 1516, and an input/output (I/O) adapter 1518. The I/O adapter 1518 can connect to peripheral devices, such as disk units 1511 and tape drives 1513, or other program storage devices that are readable by the system. The system can read the inventive instructions on the program storage devices and follow these instructions to execute the methodology of at least one embodiment of the invention. The system further includes a user interface adapter 1519 that connects a keyboard 1515, mouse 1517, speaker 1524, microphone 1522, and/or other user interface devices such as a touch screen device (not shown) to the bus 1512 to gather user input. Additionally, a communication adapter 1520 connects the bus 1512 to a data processing network 1525, and a display adapter 1521 connects the bus 1512 to a display device 1523 which may be embodied as an output device such as a monitor, printer, or transmitter, for example.

The flowchart and block diagrams in the figures illustrate the architecture, functionality, and operation of possible implementations of systems, methods and computer program products according to various embodiments of the present invention. In this regard, each block in the flowcharts or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the root terms "include" and/or "have", when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means plus function elements in the claims below are intended to include any structure, or material, for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

Although the present invention has been described in terms of particular example embodiments, it is not limited to those embodiments. The embodiments, examples, and modifications which would still be encompassed by the invention may be made by those skilled in the art, particularly in light of the foregoing teachings.

As used above "in fluid communication" is intended to indicate that two components are in fluid communication with each other and that fluid is able to pass from one component to another component directly or indirectly.

As used above "substantially," "generally," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

Those skilled in the art will appreciate that various adaptations and modifications of the exemplary and alternative embodiments described above can be configured without departing from the scope and spirit of the invention. Therefore, it is to be understood that, within the scope of the appended claims, the invention may be practiced other than as specifically described herein.

VI. INDUSTRIAL APPLICABILITY

An oro-nasal inhalation plethysmography mask exposure system is provided. The provided systems and methods are particularly suited for providing a plenum in fluid communication with an inhalation source, and a challenge plethysmography mask in fluid communication with the plenum. A processor is configured to process an output signal of a pressure sensor into respiratory data for each test animal during an exposure study.

The invention claimed is:

1. A system comprising:

an inhalation source;

a plenum in fluid communication with said inhalation source;

at least one challenge plethysmography mask in fluid communication with said plenum, each challenge plethysmography mask including a mask having a cavity in which to receive at least a nose of a test animal, a delivery conduit in fluid communication with said plenum and the cavity of said mask, at least one exhaust conduit in fluid communication between the cavity of said mask and said plenum, and a pressure sensor attached to said mask to measure pressure within the cavity of said mask;

at least one sampling mask in fluid communication with said plenum, each sampling mask including a cavity, a sealing wall covering an open side of said sampling mask, and a sampling conduit passing through said sealing wall and placing a sampling end at a point inside the cavity of said sampling mask and an attachment end external to said sampling mask;

at least one processor in electrical communication with said at least one pressure sensor, said processor configured to process an output signal of said pressure sensor into respiratory data for each test animal during an exposure study; and an exhaust system in fluid communication with said plenum.

2. The system according to claim 1, further comprising at least one sampling mask system including:

said at least one sampling mask;

an aerosol diluter/APS in fluid communication with said at least one sampling mask and in electrical communication with said at least one processor; and wherein said at least one sampling mask system is in fluid communication with said plenum and in electrical communication with said at least one processor.

3. The system according to claim 2, wherein said at least one sampling mask system includes a concentration sampling mask in fluid communication with said plenum;

an aerosol sampler in fluid communication with said concentration sampling mask;

at least one filter in fluid communication with said aerosol sampler and said exhaust system.

4. The system according to claim 2, wherein said at least one sampling mask includes a delivery conduit in fluid communication with said plenum and the cavity of said sampling mask, and a pair of exhaust conduits in fluid communication between the cavity of said sampling mask and said plenum, said exhaust conduits are located on opposing surfaces of said sampling mask.

5. The system according to claim 1, wherein said inhalation source includes a compressed gas source;

a gas flow controller in fluid communication with said compressed gas source; and a nebulizer in fluid communication with said gas flow controller and said plenum.

6. The system according to claim 5, wherein said inhalation source further includes a second gas flow controller in fluid communication with said compressed gas source; and a radial mixer in fluid communication with said nebulizer, said second gas flow controller and said nebulizer such that the gas flows from said nebulizer and said second gas flow controller are mixed together prior to discharge towards said plenum.

7. The system according to claim 1, wherein said inhalation source further includes a diffusion dryer in fluid communication with said plenum such that the gas flow from said inhalation source passes through it prior to entry into said plenum.

8. The system according to claim 1, wherein said exhaust system includes at least one filter in fluid communication with said plenum;

an exhaust gas flow controller in fluid communication with said plenum such that said exhaust gas flow controller regulates the flow rate exiting said plenum; and a vacuum in fluid communication with said exhaust gas flow controller to draw the exiting gas flow from said plenum.

9. The system according to claim 1, wherein said exhaust system includes an exhaust sink having a reservoir to at least one of kill organic inhalants and neutralize organic inhalants.

10. The system according to claim 1, wherein each challenge plethysmography mask having two exhaust conduits attached on opposing surfaces of said mask.

11. The system according to claim 10, wherein said two exhaust conduits from a Y-shaped conduit such that said stem of the Y is in fluid communication with said plenum.

12. The system according to claim 1, wherein said at least one challenge plethysmography mask includes a dental dam over at least a portion of an open side of said mask and partially enclosing the cavity of said mask.

13. A sampling mask for use in an exposure system, said sampling mask comprising:

a mask having an open ended cavity, a sealing wall covering the cavity of said mask, a sampling conduit passing through said sealing wall and placing a sampling end at a point inside the cavity and an attachment end external to said sampling mask, a delivery conduit connectable to a plenum and in fluid communication with the cavity of said mask, at least one exhaust conduit in fluid communication with the cavity of said mask and connectable to the plenum, and a pressure sensor attached to said mask to measure pressure within the cavity of said mask.

14. A method for performing an exposure study of at least one test animal using an exposure system, the method comprising:

placing a snout of one test animal into a challenge plethysmography mask having a delivery conduit connecting the mask to a plenum, at least one exhaust conduit connecting the mask to the plenum, and a pressure sensor on the mask to measure a pressure within a cavity of the mask;

creating an environment within the plenum having material provided by an inhalation source where the material is being used in the exposure study;

passing the environment through the delivery conduit to the mask; passing the environment in the mask including expiration from the test animal through the at least one exhaust conduit back to the plenum;

sending a pressure signal from the pressure sensor to a processor;

sampling characteristics of the environment present in the plenum, wherein the sampling is taken from a cavity of a sampling mask having a delivery conduit connecting the sampling mask to the plenum, two exhaust conduits connecting the sampling mask to the plenum, a sealing wall over an open face of the sampling mask, and a sampling conduit passing through the sealing wall and through which the sampling is taken; and calculating, with the processor connected to the pressure sensor, a dosage received by the test animal based on respiration data obtained from the pressure signal provided by the pressure sensor and environment characteristics.

15. The method according to claim 14, wherein sampling characteristics includes sampling a concentration of a material being used in the exposure study.

16. The method according to claim 14, wherein calculating the dosage includes calculating the respiratory frequency for the test animal based on the pressure signal from the pressure sensor, calculating a minute volume based on the respiratory frequency and a tidal volume, correlating the characterization data for the environment with the respiratory information, and determining the dosage received by the test animal.

17. The method according to claim 14, wherein the characterization data includes particle size for the material.

18. The method according to claim 14, further comprising:

creating the environment using a nebulizer attached to a compressed gas source; and pulling the environment from the plenum using a vacuum.

19. The system according to claim 1, wherein said plenum includes a housing having a cavity in fluid communication with said inhalation source and said exhaust system; and a plurality of connection ports in fluid communication with and configured to attach to any of said delivery conduit and said exhaust conduit to establish fluid communication from said plenum cavity to said connected delivery conduit or exhaust conduit.

* * * * *